US00PP26897P2

(12) United States Plant Patent
Kordes

(10) Patent No.: US PP26,897 P2
(45) Date of Patent: Jul. 5, 2016

(54) MINIATURE ROSE PLANT NAMED 'KORPOT053'

(50) Latin Name: *Rosa hybrida*
Varietal Denomination: KORpot053

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co. KG, Offenseth-Sparrieshoop (DE)

( * ) Notice: Subject to any disclaimer, the term of this patent is extended or adjusted under 35 U.S.C. 154(b) by 131 days.

(21) Appl. No.: 13/999,855

(22) Filed: Mar. 27, 2014

(51) Int. Cl.
*A01H 5/02* (2006.01)

(52) U.S. Cl.
USPC ..... Plt./118

(58) Field of Classification Search
USPC ..... Plt./118
See application file for complete search history.

*Primary Examiner* — Keith Robinson

(57) ABSTRACT

A new and distinct variety of rose with long lasting, novel orange-red flowers, and attractive foliage with very good disease resistance. It exhibits a compact to bushy growth habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot053'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a miniature rose plant which was discovered in a cultivated area in my nursery Jun. 1, 2011. The new rose variety resulted from a naturally occurring mutation of unknown causation on a branch of 'KORemopea', a non-patented rose variety from the same inventor.

The new rose plant was asexually propagated for further evaluation. This new and distinctive miniature rose variety is named 'KORpot053'.

SUMMARY OF THE DISCOVERY

The new rose plant may be distinguished from 'KORemopea' by its orange-red flowers.

The new and distinct rose plant was selected due to it its:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot053' from all other varieties of which we are aware.

As part of the rose evaluation program, Tim-Hermann Kordes asexually propagated the mutation by rooting cuttings, and conducted evaluations and observations on the resulting plants in a controlled environment in Offenseth-Sparrieshoop, Germany. The resulting seedlings exhibited distinctive physical and biological characteristics. The first asexual reproduction of 'KORpot053' was done by rooting softwood cuttings in a controlled environment in June 2011.

These initial and other subsequent propagations conducted in controlled environments show that the foregoing and all other characteristics of 'KORpot053' come true to form and are transmitted through succeeding generations.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot053' of plants of 6 months of age in a nursery in Oregon.

DETAILED BOTANICAL DESCRIPTION

The following is a description of 'KORpot053', as observed growing in July 2013 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORemopea' and 'KORamgat', a patented variety from the same breeder—U.S. Plant Pat. No. 15,612 with issue date of Mar. 1, 2005 are compared to 'KORpot053' in Chart 1.

CHART 1

| Characteristic | 'KORpot053' | 'KORemopea' | 'KORamgat' |
|---|---|---|---|
| Bud color | As sepals first unfold, bud color is Yellow Group 12B with Orange-Red Group 34B tip. | As sepals first unfold, bud color is Orange Group 25C and Orange 25D. | Yellow-Orange Group 20B. |
| Color Upon Opening, Outermost Petals, Inner Side | Yellow Group 13A with Orange Group 26A and Orange Group 26B edges. | Yellow Group 13B. | Yellow Group 6B. |
| Color Upon Opening, Innermost Petals, Inner Side | Basal zone: Yellow Group 12A; Middle zone: Yellow-Orange Group 15A; Marginal zone: Orange-Red Group 31A. | Yellow Group 13B. | Yellow Group 13B. |

Parents:

*Parent*.—'KORemopea'.

Classification:

*Botanical classification*.—*Rosa hybrida* 'KORpot053'.

*Commercial classification*.—Miniature rose.

FLOWER AND FLOWER BUD

Blooming habit: Recurrent.

Flower bud:

*Size*.—Upon opening, 27 mm in length from base of receptacle to distal end of bud and 15 mm diameter at its widest point.

*Bud form*.—Long. Pointed ovoid.

*Bud color*.—As sepals first unfold, bud color is Yellow Group 12B with Orange-Red Group 34B tip. When ¼ open, the upper surface of petals is Yellow Group 13A with Orange Group 25B edges, and the lower surface is Yellow Group 13B with Orange-Red Group 30D edges.

*Sepals*.—Color: Upper surface Green Group 138A. Lower surface Yellow-Green Group 144A. Size: Average 30-34 mm (l)×7-8 mm (w). Shape: Moderate foliaceous appendages on 3 of the five sepals. Apex: Cirrose. Base: Flat at union with receptacle. Quantity: Five. Surface texture: Upper side: A few fine hairs present. Lower surface: Very pubescent. Margins: With stipitate glands.

Flower bloom:

*Fragrance*.—Very light.

*Duration*.—On the plant 16-22 days. Senesced petals clinging.

*Size*.—Large for a miniature rose. When open, the average flower diameter is 50-60 mm and the average flower height is 25-30 mm.

*Form*.—Shape of flower when viewed from the side: Upon opening, upper part: Flattened convex. Upon opening, lower part: Flattened convex. Open flower, upper part: Flattened convex. Open flower, lower part: Concave.

Color:

*Upon opening, petals*.—Outermost petals: Outer Side: Yellow Group 7B with Orange-Red Group 30A edges. Inner Side: Yellow Group 13A with Orange Group 26A and Orange Group 26B edges. Innermost petals: Outer Side: Basal zone: Yellow Group 7A; Middle zone: Orange Group 26A; Marginal zone: Orange-Red Group 34A. Inner Side: Basal zone: Yellow Group 12A; Middle zone: Yellow-Orange Group 15A; Marginal zone: Orange-Red Group 31A.

*Upon opening, basal petal spots*.—Average Size: 6-8 mm (h)×6-8 mm (w). Basal petal spot, outermost petals: Outer Side: Yellow-Green Group 151C. Inner side: No distinctive coloration at petal base observed. Basal petal spot, innermost petals: No distinctive coloration at petal base observed.

*After opening, petals*.—Outermost petals: Outer Side: Yellow Group 12A with Orange-Red Group 31A edges. Inner Side: Yellow Group 13A with Orange Group 26B edges. Innermost petals: Outer Side: Yellow Group 7A with Orange-Red Group 30B edges. Inner Side: Yellow Group 13A with Orange-Red Group 31A edges.

*After opening, basal petal spots*.—No distinctive coloration at petal base observed.

General tonality: On open flower, Orange-Red Group 30B. No change in the general tonality at the end of the $10^{th}$ day. Afterwards, general tonality is Orange-Red Group 32C.

Petals:

*Petal type*.—Double.

*Petal count*.—Approximately 30-35 petals per flower under normal conditions.

*Petal reflex*.—Petals reflex slightly.

*Petal margin*.—Entire.

*Petal shape*.—Obovate.

*Petal size*.—20-25 mm (l)×20-23 mm (w).

*Petal arrangement*.—Not formal.

*Texture*.—Outer Side: Smooth. Inner Side: Smooth.

Petaloids:

*Petaloid count*.—Average of 8-10 per flower.

*Petaloid size*.—10-15 mm (l)×5-10 mm (w).

*Petaloid color*.—Inner side: Yellow-Orange Group 14A with Orange Group 24A edges. Outer side: Yellow-Orange Group 14B with Orange-Red Group 30A edges.

*Petaloid texture*.—Outer Side: Smooth. Inner Side: Smooth.

*Margins*.—Undulated.

*Petaloid shape*.—Most commonly spatulate with some petaloids highly irregular. Apex: Obtuse. Base: Attenuate.

Reproductive organs:

*Pistils*.—Average. Approximately 20-25 present. Stigmas: Location: Slightly superior in position to anthers. Color: Greyed-Yellow Group 160C. Styles: Length: About 10 mm long. Color: Greyed-Red Group 182D. Ovary: Length: 3.0 mm. Diameter: 1.5 mm. Color: Yellow-Green Group 145D.

*Stamens*.—Approximately 45-50 on average and regularly arranged. Anthers: Size: Average 3 mm (l)×1.5 mm (w). Color: Yellow Group 12C. Pollen: Moderate amounts generally present. Color: Yellow Group 13A. Filaments: Color: Yellow Group 13A. Length: 6 mm.

Receptacle:

*Surface*.—A few fine hairs.

*Color*.—Yellow-Green Group 144A.

*Shape*.—Urn-shaped.

*Texture*.—Smooth.

*Size*.—7-8 mm (h)×5-6 mm (w).

Peduncle:

*Surface*.—Lacking fine hairs and stipitate glands.

*Length*.—55-65 mm average length.

*Diameter*.—2.5-3 mm average diameter.

*Color*.—Yellow-Green Group 144A.
*Strength*.—Somewhat strong.
*Texture*.—Smooth.
*Borne*.—Singularly. Occasionally up to 4 flowers per stem. Flowers held upright.

Inflorescence:
*Type*.—Solitary.
*Flowering laterals*.—Below initiation of inflorescence, occasionally 1-3 flowering laterals are present. When flowering laterals are present, there is 1 flower per flowering lateral.

THE PLANT

Growth: Moderately vigorous.

Plant habit: Compact to bushy habit. When grown as a 15 cm pot plant, the average plant height is 25-30 cm and the average plant width is 20-25 cm.

Stems:
*Stem color*.—Yellow-Green Group 144A.
*Stem surface texture*.—Smooth.

Prickles: Present.
*Incidence*.—Average of 5-7 per each 10 cm of stem.
*Size*.—Average length: 5 mm.
*Color*.—Yellow-Green Group 145A.
*Shape*.—Linear to concave.
*Texture*.—Smooth.
*Anthocyanin*.—Greyed-Red Group 180C.

Leaves: Normally 5 leaflets on normal leaves in middle of the stem.
*Venation pattern*.—Pyramidal net pattern.
*Leaf size*.—90-100 mm (l)×65-75 mm (w).
*Shape*.—Elliptic.
*Abundance*.—Very abundant.
*Texture*.—Upper side of leaflet: Semi-glossy. Lower side of leaflet: Matte.

Leaflets:
*Size*.—Average size of the terminal leaflet is 40-50 mm (l)×25-30 mm (w).
*Shape*.—Elliptic. Base: Obtuse. Apex: Acute.
*Margins*.—Serrated.
*Surface*.—Upper side of leaflet: Semi-glossy. Lower side of leaflet: Matte.
*Texture*.—Leathery.
*Color, mature foliage*.—Upper Leaflet Surface: Green Group 137A. Lower Leaflet Surface: Green Group 137C.
*Color, juvenile foliage*.—Upper Leaflet Surface: Green Group 138A. Lower Leaflet Surface: Green Group 138B.
*Anthocyanin intonation*.—Greyed-Purple Group 185A. Location: Upper and lower surface of juvenile foliage.
*Arrangement*.—Odd pinnate.
*Venation*.—Reticulate.

Stipules:
*Size*.—15 mm (l)×5-6 mm (w).
*Stipule color*.—Green Group 137A.
*Stipitate glands*.—Present along margins.
*Texture*.—Smooth.
*Shape*.—Apex: Apiculate. Base: Flat.

Petiole:
*Length*.—Average 15 mm.
*Diameter*.—Average 1.5 mm.
*Petiole color*.—Green Group 137B. Underneath: Green Group 137D.
*Margins*.—With stipitate glands.
*Prickles*.—Occasionally present underneath.
*Stipitate glands*.—Limited.
*Texture*.—Smooth.

Petiole rachis:
*Length*.—Average 30-35 mm.
*Diameter*.—Average 1-1.5 mm.
*Color*.—Green Group 137B.
*Margins*.—With stipitate glands.
*Prickles*.—A few small prickles underneath.

Roots:
*Type*.—Fibrous.
*Color*.—Greyed-Orange Group 165A.

Hips/seed formation: None observed.

Winter hardiness: Due to the variety's principal use in greenhouses, winter hardiness has not been evaluated.

Disease resistance: Very good resistance to powdery mildew and *Botrytis* under normal growing conditions in Jackson County, Oreg. greenhouse.

I claim:

1. A new and distinct variety of rose plant, as described and illustrated herein.

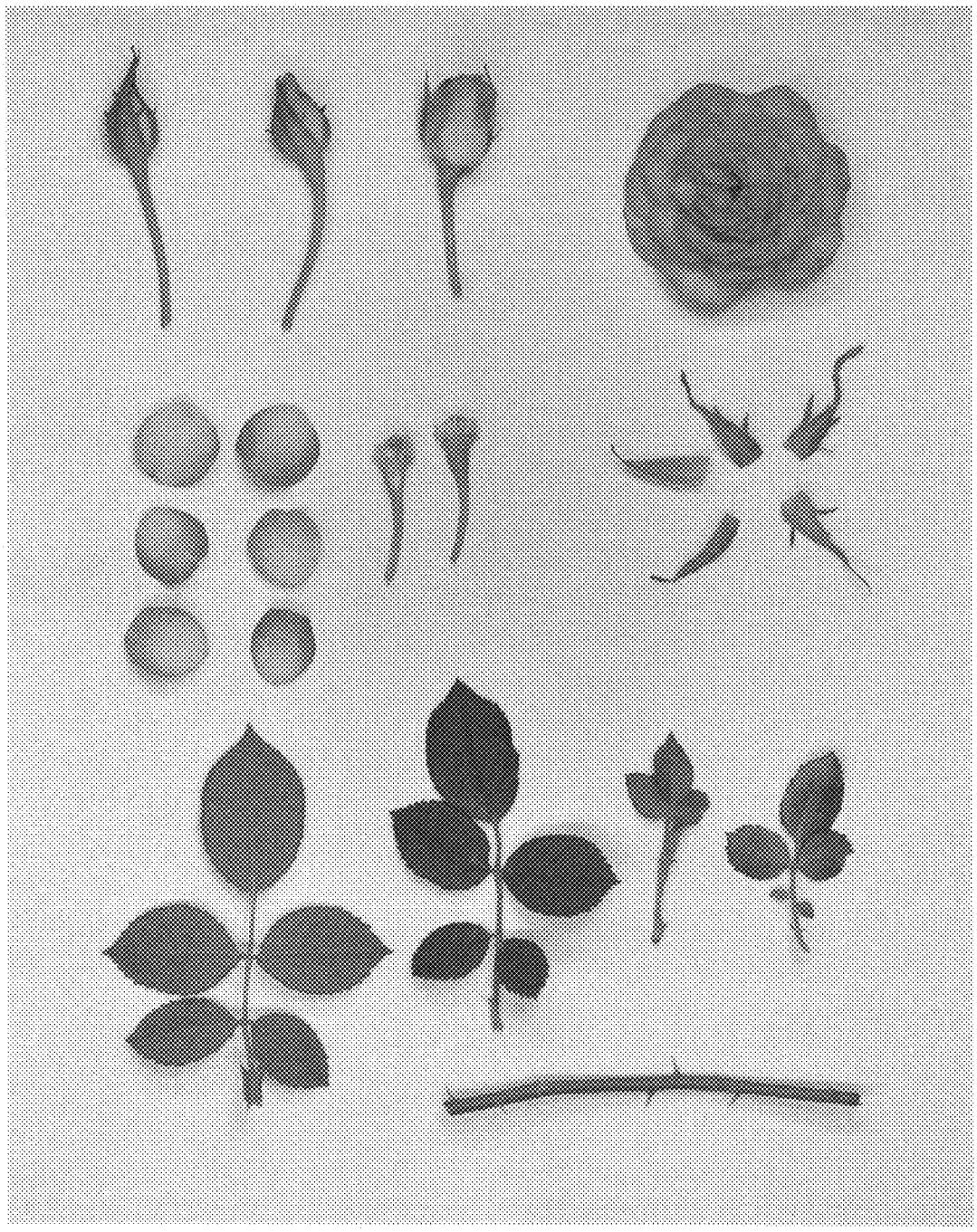

* * * * *